United States Patent
Yamazaki

(10) Patent No.: US 6,967,207 B2
(45) Date of Patent: Nov. 22, 2005

(54) PREVENTIVE OR THERAPEUTIC AGENTS FOR GASTRIC OR ESOPHAGEAL REGURGITATION

(75) Inventor: Satoshi Yamazaki, Tokyo (JP)

(73) Assignee: Mitsubishi Pharma Corporation, Osaka (JP)

( * ) Notice: Subject to any disclaimer, the term of this patent is extended or adjusted under 35 U.S.C. 154(b) by 248 days.

(21) Appl. No.: 10/203,278

(22) PCT Filed: Feb. 7, 2001

(86) PCT No.: PCT/JP01/00852

§ 371 (c)(1),
(2), (4) Date: Nov. 8, 2002

(87) PCT Pub. No.: WO01/58898

PCT Pub. Date: Aug. 16, 2001

(65) Prior Publication Data

US 2003/0130304 A1 Jul. 10, 2003

(30) Foreign Application Priority Data

Feb. 9, 2000 (JP) ........................ 2000-031542

(51) Int. Cl.$^7$ .............................................. A61K 31/44
(52) U.S. Cl. ...................................................... 514/301
(58) Field of Search ......................................... 514/301

(56) References Cited

U.S. PATENT DOCUMENTS 5,352,685 A 10/1994 Maruyama et al. ......... 514/301

FOREIGN PATENT DOCUMENTS

EP 560348 9/1993

OTHER PUBLICATIONS

CA 132:117101, Revel et al, Drugs of the Future 1999 24(9) 966–968, abstract.*
B. Johansen et al., "BRL 24924, a 5–Hydroxytryptamine Type 3 Antagonist•••and Pepsin in vitro", Digestion, 1991, vol. 48, No. 3, pp. 121–127.

* cited by examiner

Primary Examiner—Rebecca Cook
(74) Attorney, Agent, or Firm—Wenderoth, Lind & Ponack, L.L.P.

(57) ABSTRACT

The compound of the following formula:

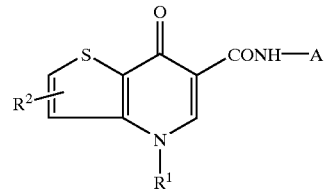

wherein $R^1$ and $R^2$ independently represent a hydrogen atom or a lower alkyl group; A represents a group selected from the group consisting of 1-azabicyclo[3.2.2]nonyl group, 1-azabicyclo[2.2.2]octyl group, or an N-oxide thereof, or a pharmaceutically acceptable salt thereof or a hydrate thereof has both improving effect on enterokinetic functions and suppressing effect on acid secretion, and also is highly safe. Accordingly, the substance is useful as preventive or therapeutic medicament for a gastroesophageal reflux disease.

5 Claims, No Drawings

PREVENTIVE OR THERAPEUTIC AGENTS FOR GASTRIC OR ESOPHAGEAL REGURGITATION

This application is a 371 of PCT/JP01/00852 filed Feb. 7, 2001.

TECHNICAL FIELD

The present invention relates to a medicament comprising thieno[3,2-b]pyridinecarboxamide derivative as an active ingredient which is useful for preventive and/or therapeutic treatment of a gastroesophageal reflux disease.

BACKGROUND ART

Gastroesophageal reflux disease (hereafter referred to as "GERD") is a generic term of diseases with various digestive symptoms such as pyrosis, acid regurgitation, obstructed admiration, aphagia, pectoralgia, permeating feeling and the like sensibility caused by reflux in the esophagus and stagnation of gastric contents, duodenal juice, bile, pancreatic juice and the like. The term covers both of reflux esophagitis in which erosion and ulcers are endoscopically observed, and esophageal regurgitation-type non-ulcer dyspepsia (NUD) in which no abnormality is endoscopically observed.

Examples of causes of GERD include intraesophageal reflux of gastric contents due to lowered contractibility of the lower esophageal sphincter, reduced resistance of esophageal mucosa to acid and/or pepsin, reduction of esophageal clearance after reflux, prolongation of gastric evacuation, esophageal hiatus hernia and the like.

For treatment of GERD, administrations of acid secretion depressors such as a histamine $H_2$ receptor antagonists and proton pump inhibitors, and/or administrations of agents for improvement of enterokinetic functions such as cisapride which improve lowered contractibility of the lower esophageal sphincter and prolongation of gastric evacuation have been mainly applied.

However, a sole administration of a single histamine H2 receptor antagonist or agent for improvement of enterokinetic functions sometimes fails to achieve satisfactory therapeutic effect. In addition, although the proton pump inhibitors can achieve high efficacy, their prolonged administrations have not been approved from a viewpoint of safety, which may arise a problem of recurrence. For these reasons, development of a medicament has been desired which can be administered for a prolonged period of time, and has a high effectiveness and reduced side effect.

An object of the present invention is to provide a medicament having high efficacy for preventive and/or therapeutic treatment of a gastroesophageal reflux disease and reduced side effect.

DISCLOSURE OF THE INVENTION

The inventors of the present invention conducted various researches to achieve the foregoing object. As a result, they found that a particular class of thieno[3,2-b]pyridinecarboxamide derivatives has both excellent improving effect on enterokinetic functions and suppressing effect on acid secretion. The present invention was achieved on the basis of the findings.

The present invention thus provides a preventive or therapeutic medicament for a gastroesophageal reflux disease which comprises as an active ingredient a thieno[3,2-b]pyridinecarboxamide derivative represented by the following formula (I) or a pharmaceutically acceptable salt thereof, or a solvate or a hydrate thereof:

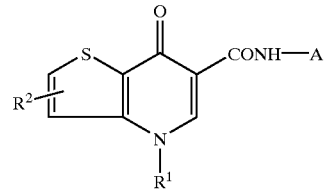

wherein $R^1$ and $R^2$ independently represent a hydrogen atom or a lower alkyl group; A represents a group selected from the group consisting of 1-azabicyclo[3.2.2]nonyl group, 1-azabicyclo[2.2.2]octyl group, or an N-oxide thereof.

According to preferred embodiments of the present invention, provided are the aforementioned preventive or therapeutic medicament, wherein $R^1$ and $R^2$ independently represent a hydrogen atom or methyl group; the aforementioned preventive or therapeutic medicament, wherein A is 1-azabicyclo[2.2.2]oct-3-yl group or an N-oxide thereof; the aforementioned preventive or therapeutic medicament, wherein each of $R^1$ and $R^2$ is a hydrogen atom and an absolute configuration of a carbon atom in the group A attached to the carboxamide group is R-configuration; and the aforementioned preventive or therapeutic medicament, wherein the active ingredient is in a form of a hydrochloride.

As an active ingredient of the preventive or therapeutic medicament of the present invention, one or more of the compounds falling within the thieno[3,2-b]pyridinecarboxamide derivative represented by the above formula. In the formula, $R^1$ and $R^2$ independently represents a hydrogen atom or a lower alkyl group. Examples of the lower alkyl group include $C_1$–$C_6$ alkyl groups such as methyl group, ethyl group, n-propyl group, i-propyl group, n-butyl group, sec-butyl group, tert-butyl group and the like, or preferably $C_1$–$C_4$ alkyl groups. Among them, methyl group is preferred. The compounds wherein each of $R^1$ and $R^2$ is a hydrogen atom are also preferred active ingredients of the medicament of the present invention. When $R^2$ represents a lower alkyl group, $R^2$ may substitute on either of 2-position or 3-position of thieno[3,2-b]pyridine ring.

In the aforementioned formula (I), A represents 1-azabicyclo[3.2.2]nonyl group or 1-azabicyclo[2.2.2]octyl group, or a group wherein the nitrogen atom of each of the aforementioned group forms N-oxide. A bond between the group A and the carboxamide group of the compound of the formula (I) is formed by any carbon atom of the group A and the nitrogen atom of the carboxamide group. Example of the group A include, for example, 1-azabicyclo[2.2.2]oct-2-yl group, 1-azabicyclo[2.2.2]oct-3-yl group, 1-azabicyclo[2.2.2]oct-4-yl group, 1-azabicyclo[3.2.2]non-2-yl group, 1-azabicyclo[3.2.2]non-3-yl group, 1-azabicyclo[3.2.2]non-4-yl group, 1-azabicyclo[3.2.2]non-5-yl group, 1-azabicyclo[3.2.2]non-6-yl group, 1-azabicyclo[3.2.2]non-7-yl group, and groups corresponding to their N-oxides.

Stereochemistry of a carbon atom in the group A that binds to the nitrogen atom of the carboxamide group is not particularly limited, and the atom may be in either R- or S-configuration. As for the group A, a racemate, or a mixture in any ratio of optical isomers may be used. When an optically active group A is used, those wherein an absolute configuration of the above carbon atom is R-configuration may preferably be used.

Among the compounds as active ingredients of the medicament of the present invention, examples of particularly preferred compounds include a racemate or any optically active isomers, or their N-oxides of:

N-(1-azabicyclo[2.2.2]oct-3-yl)-4,7-dihydro-7-oxo-thieno[3,2-b]pyridine-6-carboxamide;
N-(1-azabicyclo[2.2.2]oct-3-yl)-4,7-dihydro-4-methyl-7-oxo-thieno[3,2-b]pyridine-6-carboxamide;
N-(1-azabicyclo[2.2.2]oct-3-yl)-4,7-dihydro-4-ethyl-7-oxo-thieno[3,2-b]pyridine-6-carboxamide;
N-(1-azabicyclo[2.2.2]oct-3-yl)-4,7-dihydro-2,4-dimethyl-7-oxo-thieno[3,2-b]pyridine-6-carboxamide;
N-(1-azabicyclo[2.2.2]oct-3-yl)-4,7-dihydro-3,4-dimethyl-7-oxo-thieno[3,2-b]pyridine-6-carboxamide;
N-(1-azabicyclo[2.2.2]oct-3-yl)-4,7-dihydro-4-ethyl-2-methyl-7-oxo-thieno[3,2-b]-pyridine-6-carboxamide;
N-(1-azabicyclo[2.2.2]oct-2-yl)-4,7-dihydro-7-oxo-thieno[3,2-b]pyridine-6-carboxamide;
N-(1-azabicyclo[2.2.2]oct-2-yl)-4,7-dihydro-4-methyl-7-oxo-thieno[3,2-b]pyridine-6-carboxamide;
N-(1-azabicyclo[2.2.2]oct-2-yl)-4,7-dihydro-4-ethyl-7-oxo-thieno[3,2-b]pyridine-6-carboxamide;
N-(1-azabicyclo[2.2.2]oct-2-yl)-4,7-dihydro-2,4-dimethyl-7-oxo-thieno[3,2-b]pyridine-6-carboxamide;
N-(1-azabicyclo[2.2.2]oct-2-yl)-4,7-dihydro-3,4-dimethyl-7-oxo-thieno[3,2-b]pyridine-6-carboxamide;
N-(1-azabicyclo[2.2.2]oct-2-yl)-4,7-dihydro-4-ethyl-2-methyl-7-oxo-thieno[3,2-b]-pyridine-6-carboxamide;
N-(1-azabicyclo[2.2.2]oct-4-yl)-4,7-dihydro-7-oxo-thieno[3,2-b]pyridine-6-carboxamide;
N-(1-azabicyclo[2.2.2]oct-4-yl)-4,7-dihydro-4-methyl-7-oxo-thieno[3,2-b]pyridine-6-carboxamide;
N-(1-azabicyclo[2.2.2]oct-4-yl)-4,7-dihydro-4-ethyl-7-oxo-thieno[3,2-b]pyridine-6-carboxamide;
N-(1-azabicyclo[2.2.2]oct-4-yl)-4,7-dihydro-2,4-dimethyl-7-oxo-thieno[3,2-b]pyridine-6-carboxamide;
N-(1-azabicyclo[2.2.2]oct-4-yl)-4,7-dihydro-3,4-dimethyl-7-oxo-thieno[3,2-b]pyridine-6-carboxamide;
N-(1-azabicyclo[2.2.2]oct-4-yl)-4,7-dihydro-4-ethyl-2-methyl-7-oxo-thieno[3,2-b]-pyridine-6-carboxamide;
N-(1-azabicyclo[3.2.2]non-2-yl)-4,7-dihydro-7-oxo-thieno[3,2-b]pyridine-6-carboxamide;
N-(1-azabicyclo[3.2.2]non-2-yl)-4,7-dihydro-4-methyl-7-oxo-thieno[3,2-b]pyridine-6-carboxamide;
N-(1-azabicyclo[3.2.2]non-2-yl)-4,7-dihydro-4-ethyl-7-oxo-thieno[3,2-b]pyridine-6-carboxamide;
N-(1-azabicyclo[3.2.2]non-2-yl)-4,7-dihydro-2,4-dimethyl-7-oxo-thieno[3,2-b]pyridine-6-carboxamide;
N-(1-azabicyclo[3.2.2]non-2-yl)-4,7-dihydro-3,4-dimethyl-7-oxo-thieno[3,2-b]pyridine-6-carboxamide;
N-(1-azabicyclo[3.2.2]non-2-yl)-4,7-dihydro-4-ethyl-2-methyl-7-oxo-thieno[3,2-b]-pyridine-6-carboxamide;
N-(1-azabicyclo[3.2.2]non-3-yl)-4,7-dihydro-7-oxo-thieno[3,2-b]pyridine-6-carboxamide;
N-(1-azabicyclo[3.2.2]non-4-yl)-4,7-dihydro-7-oxo-thieno[3,2-b]pyridine-6-carboxamide;
N-(1-azabicyclo[3.2.2]non-5-yl)-4,7-dihydro-7-oxo-thieno[3,2-b]pyridine-6-carboxamide;
N-(1-azabicyclo[3.2.2]non-6-yl)-4,7-dihydro-7-oxo-thieno[3,2-b]pyridine-6-carboxamide; and
N-(1-azabicyclo[3.2.2]non-7-yl)-4,7-dihydro-7-oxo-thieno[3,2-b]pyridine-6-carboxamide. However, the active ingredients of the medicaments of the present invention are not limited to these compounds.

Among them, most preferred compounds are R-(−)-N-(1-azabicyclo[2.2.2]oct-3-yl)-4,7-dihydro-7-oxo-thieno[3,2-b]pyridine-6-carboxamide [also referred to as (R)-N-(3-quinuclidinyl)-7-oxo-4,7-dihydrothieno[3,2-b]pyridine-6-carboxamide] or N-oxide thereof. When $R^1$ represents a hydrogen atom in the aforementioned formula (I), 4,7-dihydro-7-oxo-thieno[3,2-b]pyridine as a heteroaromatic ring moiety may also exist as a tautomer thereof, i.e., 7-hydroxythieno[3,2-b]pyridine. Such tautomers also fall within the active ingredients of the medicament of the present invention.

Methods for preparation of the aforementioned compounds are described in Japanese Patent Unexamined Publication (KOKAI) No. 5-310747 (EP560348).

As an active ingredient of the medicament of the present invention, pharmaceutically acceptable salts of the aforementioned compounds may be used. Examples of the salts include acid addition salts, quaternary ammonium salts and the like. Examples of the pharmaceutically acceptable acid addition salts include, for example, inorganic acid salts such as hydrochlorides, hydrobromides, hydroiodides, sulfates, phosphates and the like, and organic acid salts such as oxalates, maleates, fumarates, lactates, malates, citrates, tartrates, benzoates, methanesulfonates and the like.

Examples of the quaternary ammonium salts include, for example, quaternary ammonium salts with lower alkyl halogenides such as methyl iodides, methyl bromides, ethyl iodides, ethyl bromides and the like, those with lower alkyl sulfonates such as methyl methanesulfonates, ethyl methanesulfonates and the like, and those with lower alkyl arylsulfonates such as methyl p-toluenesulfonates and the like. The compounds represented by the formula (I) or pharmaceutically acceptable salts thereof may exist as hydrates. These hydrates may be used as active ingredients of the medicament of the present invention.

Japanese Patent Unexamined Publication (KOKAI) No. 5-310747 discloses enhancing effect of the aforementioned compound on stomach motility, more specifically, enhancing action on stomach evacuation in male ddy mice, enhancing action on constriction of a dog stomach sewed with a strain gauge transducer, and an antagonistic action on a 5-$HT_3$ (serotonin 3) receptor demonstrated by the Bezold-Jarish reflective test. However, the publication neither suggests nor teaches a relation between the aforementioned compound and acid secretion.

Japanese Patent Unexamined Publication (KOKAI) No. 8-143573 discloses that the aforementioned compound promotes transportation of intestinal contents by stimulating peristalsis of the stomach and small intestine, more specifically, promoting action on constricting motility of the vestibular stomach, duodenum, jejunum, and ileum of a dog, and promoting action on mouse large intestine transportation, and further a result of observation of general conditions of mice indicating the safety of the aforementioned compound. However, the publication neither suggests nor teaches a relation between the aforementioned compound and acid secretion.

It is preferred that a pharmaceutical composition is prepared by adding a pharmaceutically acceptable carrier to the aforementioned compound, a pharmaceutically acceptable salt thereof, or a hydrate thereof as an active ingredient of the medicament of the present invention. As the medicament of the present invention, a substance, per se, that is selected from the group consisting of the alkylenedioxybenzene derivative and a pharmaceutically acceptable salt thereof, and a hydrate thereof and a solvate thereof may be administered to a mammal including human. However, it is generally preferable to prepare a pharmaceutical composition comprising one or more of the aforementioned substances as an active ingredient and one or more of pharmaceutical additives and administer the composition to a patient.

Examples of the pharmaceutical composition include formulations for oral administration such as tablets, capsules, subtilized granules, powders, pills, troches, sublingual tablets and liquid preparations, and formulations for parenteral administration such as injections, suppositories, ointments, patches and the like.

Tablets and capsules for oral administration are usually provided in a unit dosage form, and can be prepared by adding ordinary pharmaceutical carriers such as binders, fillers, diluents, compressing agents, lubricants, disintegrating agents, coloring matters, flavoring agents, and moistening agents. Tablets may be coated according to a well known method, for example, by using an enteric coating agent. For example, fillers such as cellulose, mannitol and lactose; disintegrating agents such as starch, polyvinylpyrrolidone, starch derivatives and sodium starchglycolate; lubricants such as magnesium stearate; moistening agents such as sodium laurylsulfate and the like may be used.

Liquid preparations for oral administration can be provided in the forms of, for example, aqueous or oily suspensions, solutions, emulsions, syrups and elixirs, as well as dried formulations that is re-dissolvable before use by water or a suitable medium. Those liquid preparations may contain ordinary additives, for example, suspending agents such as sorbitol, syrups, methylcellulose, gelatin, hydroxyethylcellulose, carboxymethylcellulose, aluminum stearate gel and hydrogenated edible fats; emulsifiers such as lecitin, sorbitan monooleate and gum arabic; non-aqueous media including edible oils such as almond oil, rectified coconut oil, oily esters (e.g., esters of glycerin), propylene glycol and ethyl alcohol; preservatives such as methyl ester, ethyl ester and propyl ester of p-hydroxybenzoic acid and sorbic acid; and usual flavoring agents and coloring matters as required.

Formulations for oral administration can be manufactured according to a method well known in the art, for example, by mixing, filling, compressing and the like. In addition, it is also possible to disperse the active ingredient in a formulation containing a large amount of filler by repetitive mixing. Formulations for parenteral administration are generally provided as unit dosage form preparations containing the compound as the active ingredient and a sterilized medium. The solution for parenteral administration may generally be prepared by dissolving the compound in a medium, subjecting the resulting solution to filtration for sterilization, filling the solution in vials or ampoules, and sealing the vials or ampoules. It is also possible to freeze the composition and fill the result in vials, and then eliminate the moisture in vacuo to improve stability. Parenteral suspensions can be prepared by substantially the same method as that applied to solutions for parenteral administration; however, the suspensions can preferably be manufactured by suspending the active ingredient in a medium, and then subjecting the result to sterilization by using ethylene oxide or the like. Furthermore, surface active agents, moistening agents and so forth may also be added so that a uniform dispersion of the active ingredient can be obtained.

Doses of the aforementioned compound as the active ingredient can be suitably decided depending on the purpose of administration, i.e., therapeutic or preventive treatment, nature of a disease to be treated or prevented, conditions, body weight, age, sexuality and the like of a patient. In an usual case, an amount of about 0.001 mg to 10 mg per day for an adult may be administered orally, or about 0.001 mg to 10 mg may be administered by intravenous administration. Such doses may be desirably administered once a day to several times a day as divided portions.

BEST MODE FOR CARRYING OUT THE INVENTION

The present invention will be more specifically explained by examples. However, the scope of the present invention is not limited to these examples. In the following examples, R-(−)-N-(1-azabicyclo[2.2.2]oct-3-yl)-7-hydroxythieno[3,2-b]-pyridine-6-carboxamide (a tautomer of (R)-(−)-N-(1-azabicyclo[2.2.2.]oct-3-yl)-4,7-dihydro-7-oxo-thieno[3,2-b] pyridine-6-carboxamide) hydrochloride (referred to as "test compound"), prepared according to the method described in Example 2 of Japanese Patent Unexamined Publication (KOKAI) No. (Hei) 5-31074, was used.

EXAMPLE 1

Suppressing Action on Gastric Acid Secretion (Histamine Stimulation)

An effect on gastric acid secretion by stimulation under awakening was studied by using (fundic pouch dog). For preparation of the fundic pouch dog, a mongrel dog after starvation overnight was subjected to sterile ventrotomy under anesthesia using sodium pentobarbital (30 mg/kg, i.v.), and a fistula was attached to a part of the corpus ventriculi. After recovery period for two weeks, the dog was fixed to the Pavlov's stand, and gastric juice was collected every 15 minutes for 4 hours under histamine stimulation (0.2 mg/kg/hr). A volume of each collected gastric juice was recorded, and the juice was titrated with 0.01N NaOH using pH automatic measuring apparatus (Radiometer Copenhagen). The test compound, encapsulated in a gelatin capsule, was orally administered one hour before histamine administration.

|  | Amount of gastric juice secretion (mEq/4 hr) |
| --- | --- |
| Control | 116.1 ± 12.3 |
| Test compound 3 μg/kg | 76.8 ± 7.4 |
| Test compound 10 μg/kg | 61.9 ± 5.5 |

Values are shown as mean ± standard error for 6 samples

EXAMPLE 2

Suppressing Action on Gastric Acid Secretion (Tetra Gastrin Stimulation)

Experiment was conducted in a similar manner as Example 1 except that the stimulating agent was replaced with tetragastrin(2 μg/kg/hr). The results are shown below.

|  | Amount of gastric juice secretion (mEq/4 hr) |
| --- | --- |
| Control | 40.1 ± 3.9 |
| Test compound 10 μg/kg | 26.7 ± 7.8 |
| Test compound 30 μg/kg | 12.9 ± 5.3 |

Values are shown as mean ± standard error for 6 samples

The test compound suppressed secretion of gastric juice by histamine and tetragastrin stimulation.

INDUSTRIAL APPLICABILITY

The medicament of the present invention has both improving effect on enterokinetic functions and suppressing effect on acid secretion, and is highly safe. Accordingly, the medicament is useful for therapeutic and/or preventive treatment of a gastroesophageal reflux disease.

The present application was filed with the claim of priority based on Japanese patent application No. 2000-31542.

What is claimed is:

1. A method for treatment of gastroesophageal reflux disease, which comprises administering to a patient in need thereof a therapeutically effective amount of a thieno[3,2-b]pyridinecarboxamide derivative represented by the following formula (I) or a pharmaceutically acceptable salt thereof, or a hydrate thereof:

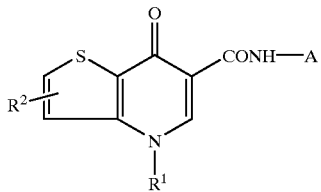

wherein $R^1$ and $R^2$ independently represent a hydrogen atom or a lower alkyl group; A represents a group selected from the group consisting of 1-azabicyclo[3.2.2]nonyl group, 1-azabicyclo[2.2.2]octyl group, or an N-oxide thereof.

2. The method according to claim 1, wherein $R^1$ and $R^2$ independently represent a hydrogen atom or methyl group, and A is 1-azabicyclo[2.2.2]oct-3-yl group or an N-oxide thereof.

3. The method according to claim 1, wherein said derivative is any one of N-(1-azabicyclo[2.2.2]oct-3-yl)-7-oxo-4,7-dihydrothieno[3,2-b]pyridine-6-carboxamide, (R)-N-(1-azabicyclo[2.2.2]oct-3-yl)-7-oxo-4,7-dihydrothieno[3,2-b]pyridine-6-carboxamide, or (S)-N-(1-azabicyclo[2.2.2]oct-3-yl)-7-oxo-4,7-dihydrothieno[3,2-b]pyridine-6-carboxamide.

4. The method according to claim 1, wherein said derivative is (R)-N-(1-azabicyclo[2.2.2]oct-3-yl)-7-oxo-4,7-dihydrothieno-[3,2-b]pyridine-6-carboxamide hydrochloride.

5. The method according to claim 1, wherein the gastroesophageal reflux disease is reflux esophagitis or regurgitation-type non-ulcer dyspepsia.

* * * * *